(12) United States Patent
Esquea et al.

(10) Patent No.: US 8,748,489 B2
(45) Date of Patent: Jun. 10, 2014

(54) SOLID PHARMACEUTICAL COMPOSITION CONTAINING A COMBINATION OF AN INTESTINAL MOTILITY REGULATING AGENT AND AN ANTIFLATULENT

(75) Inventors: Marta Luz Torres Esquea, Barranquilla (CO); Raul Bello Vergara, Barranquilla (CO)

(73) Assignee: Procaps SAS, Barranquilla (CO)

( * ) Notice: Subject to any disclaimer, the term of this patent is extended or adjusted under 35 U.S.C. 154(b) by 1281 days.

(21) Appl. No.: 11/527,501

(22) Filed: Sep. 27, 2006

(65) Prior Publication Data

US 2008/0038336 A1 Feb. 14, 2008

(30) Foreign Application Priority Data

Aug. 10, 2006 (CO) .................................. 06-078456

(51) Int. Cl.
*A01N 37/44* (2006.01)
*A01N 55/10* (2006.01)

(52) U.S. Cl.
USPC ........................................... 514/540; 514/63

(58) Field of Classification Search
USPC .................................................. 514/63, 540
See application file for complete search history.

(56) References Cited

U.S. PATENT DOCUMENTS

| 5,248,505 A * | 9/1993 | Garwin ......................... 424/472 |
| 2005/0004155 A1* | 1/2005 | Boyd et al. .................... 514/282 |

FOREIGN PATENT DOCUMENTS

| EP | 0891776 A1 * | 1/1999 |
| EP | 0806949 B1 * | 8/2003 |
| WO | WO-95/01803 * | 1/1995 |
| WO | WO-96/23493 * | 8/1996 |

* cited by examiner

*Primary Examiner* — Ali Soroush
(74) *Attorney, Agent, or Firm* — Isaac A. Angres

(57) ABSTRACT

This invention relates to a solid pharmaceutical composition that include a regulating agent of digestive and/or intestinal motility which has an agonist effect on peripheral μ, δ and κ opiate receptors; and an antiflatulent for the treatment and regulation of intestinal motility and flatulence in mammals. More in particularly, the pharmaceutical composition includes: (a) at least a regulating agent of intestinal motility such as trimebutine; (b) at least an antiflatulent such as simethicone; (c) at least a flowability promoter; (d) one or more lubricant; (e) at least an extender/diluent; (f) at least a disintegrant; and, (g) at least a binder.

15 Claims, No Drawings

SOLID PHARMACEUTICAL COMPOSITION CONTAINING A COMBINATION OF AN INTESTINAL MOTILITY REGULATING AGENT AND AN ANTIFLATULENT

This application claims priority from Colombian Patent Application No. 06-078456 filed Aug. 10, 2006, which is hereby incorporated in its entirety by reference herein.

FIELD OF THE INVENTION

The present invention relates to compositions and methods for treating and/or preventing lower gastrointestinal (GI) disorders in mammalian patients, more particularly for alleviating and/or preventing the lower GI symptoms associated with such disorders. The present invention further relates to methods for preventing and/or treating functional bowel disorders and more particularly the invention concerns the use of trimebutine [2-dimethylamino-2-phenylbutyl 3,4,5-trimethoxybenzoate hydrogen maleate], stereoisomers of trimebutine and metabolites thereof, in combination with simethicone for preventing and/or treating functional bowel disorders.

BACKGROUND OF THE INVENTION

Healthy digestion requires coordinated movements of the stomach and intestines to mix food with digestive enzymes, to stir the nutrients so they approach the intestinal wall for absorption into the body, and to propel the intestinal contents through the digestive tract. The movement of the walls of the gastrointestinal (GI) tract and their contents is called gastrointestinal motility. Gastrointestinal motility is controlled by the nerves and muscles within the gastrointestinal tract.

The normal patterns of the nerves and muscles are influenced every day by many factors. Sleeping and waking changes motility, as does exercise. Emotional distress can also have profound effects on gastrointestinal motility. Even the food that you eat releases substances into the blood which influence motility. Nerve connections between the brain and the GI tract send messages in both directions. These modify not only GI motility, but also perceptions from the gut.

Motility disorders occur when the nerves in the gastrointestinal tract are missing, immature, or damaged by infections or toxins. Disorders can also occur when the nerves are adversely influenced by chemical substances from inside the body (such as the chemicals released during an inflammation caused by Crohn's disease), or outside the body (such as opiates given for pain). In this case, the nerves and muscles of the GI tract do not function in a strong or coordinated fashion. Motility disorders may also occur when the GI muscles are diseased—either from a genetic defect (such as some forms of muscular dystrophy) or an acquired disorder (such as progressive systemic sclerosis and amyloidosis). In this case, the coordinated contractions produced by the GI muscles are too weak to move the intestinal contents.

Symptoms soon arise when there are abnormalities in the strength or coordination of contractions. Sometimes the symptoms are accompanied by evidence of growth failure or tissue damage. The symptoms may vary depending on the location and severity of the abnormalities. Heartburn and constipation are common symptoms of motility disorders. Other frequent complaints include: chronic vomiting, nausea, cramping, bloating, abdominal distention and diarrhea after eating.

The most common motility disturbance is a troublesome but relatively benign condition called "irritable bowel syndrome" (IBS). It accounts for 50 percent of all patients who see a GI specialist.

The primary function of the gastrointestinal tract is to absorb ingested nutrients. This is achieved when transit along the esophagus and gastrointestinal tract is at a rate which facilitates optimal digestion and absorption of water and electrolytes. Abnormal patterns in gastrointestinal motility result in number of disorders ranging from diffuse esophageal spasm (an esophageal obstructive disorder by dysphagia), achalasia (an obstructive disorder in which the lower esophageal sphincter fails to relax adequately resulting in dysphagia) and pain due to functional bowel disorders such as irritable bowel syndrome (IBS), non-ulcer dyspepsia, and idiopathic constipation.

Gastrointestinal distress presents itself as discomfort associated with an intestinal disorder by symptoms of diarrhea and flatulence or gas. Diarrhea is the abnormally frequent passage of watery stool. Diarrhea may have a variety of causes including bacteria or viral induced diarrhea. Travelers diarrhea, for example, is also believed to be of microbial origin. Diarrhea may also be a side effect of drug administration, particularly antibiotics. Diarrhea may be induced by food intolerance which is caused by allergy or the ingestion of foods that are excessively fatty, spicy, or contain a high degree of fermentable carbohydrate, roughage or a large number of seeds. Food intolerance may also be brought on by a preformed toxin in the food thus causing food poisoning. Other conditions and diseases can also cause diarrhea, and diarrhea may only be one of many symptoms associated with a major illness.

Diarrhea is thus a symptom of an intestinal disorder or other bodily function and symptomatic relief can be accomplished by the use of various prescription and nonprescription products. The active ingredients in these products include trimebutine, loperamide, attapulgite, bismuth subsalicylate, diphenoxylate HCl, polycarbophil, calcium polycarbophil and mixtures thereof.

Flatulence or intestinal gas is another intestinal disorder which contributes to gastrointestinal distress. Such gas exists as trapped gas bubbles which manifest itself by feelings of pain, bloating and cramping in the abdominal area.

While various products exist for treating diarrhea and gas simultaneously, no product has heretofore been proposed for treating the combination of the symptoms of both diarrhea and gas which contains trimebutine in combination with simethicone.

Trimebutine belongs to the class of medications called spasmolytics and it is a noncompetitive spasmolytic. Trimebutine is a prokinetic agent that acts directly on the smooth muscle of the GI tract and it is known to regulate abnormal intestinal activity. It is used to treat irritable bowel syndrome (spastic colon). This condition is caused by overactive movements of the bowels. Trimebutine works by slowing down the movements of the bowel. The actions of trimebutine [3,4,5-trimethoxybenzoic acid 2-(dimethylamino)-2-phenylbutylester] on the gastrointestinal tract are mediated via (i) an agonist effect on peripheral μ, δ and κ opiate receptors and (ii) release of gastrointestinal peptides such as motilin and modulation of the release of other peptides, including vasoactive intestinal peptide, gastrin and glucagon. Trimebutine accelerates gastric emptying, induces premature phase III of the migrating motor complex in the intestine and modulates the contractile activity of the colon. Recently, trimebutine has also been shown to decrease reflexes induced by distension of the gut lumen in animals and it may therefore modulate visceral sensitivity. Clinically, trimebutine has proved to be effective in the treatment of both acute and chronic abdominal pain in patients with functional bowel disorders, especially irritable bowel syndrome, at doses ranging from 300 to 600 mg/day. It is also effective in children presenting with abdominal pain.

Additionally, trimebutine has been used in many countries since 1969 for the treatment of functional bowel disorders, including irritable bowel syndrome (IBS). The efficacy of the compound to relieve abdominal pain has been demonstrated in various clinical studies using different protocols of treatment. Trimebutine given either intravenously or orally delays the appearance of a phase III of the migrating motor complex (MMC) in the stomach and the duodenum by inducing a premature phase III, migrating along the whole intestine. In man, trimebutine stimulates intestinal motility in both fed and fasted states. More recently, trimebutine has been shown to be able to influence the activity of visceral afferents by decreasing the intensity of the recto-colonic reflex in rats as evidenced by the inhibition of colonic motility consecutive to rectal distension. This result may be related to the beneficial effects found with trimebutine in patients with IBS and more specifically in the treatment of attacks of abdominal pain.

Trimebutine is a medicine that acts on the peripheral encephalinergic receptors, specially digestive receptors and therefore it is a regulator of digestive motility. Normally, trimebutine is administered in solid form, injectable dissolution, suppository and reconstitutable powder for preparation of a drinkable suspension. Another form of trimebutine includes prolonged release which has been the object of French Patent No FR 2,640,876. The oral forms of trimebutine are indicated in the treatment of pains related to functional distress, the alimentary canal and the biliary routes, as well as in the treatment of pain or intestinal functional distress. Among the proposed oral forms, the drinkable suspension is more particularly adapted to pediatric use.

On the other hand, simethicone has been used in diverse therapeutic liquid and solid forms of metering. Most of the normal formulations of metering of simethicone are antacid diverse combinations of simethicone with separated. According to it, it is necessary to separate simethicone of the antacid to avoid the inactivación of simethicone. Other formulations of simethicone in the literature have been suggested such as simethicone and dextromethorphan, as well as a combination of simethicone, a tranquilizer and an antacid. According to the prior art, it is possible to combine simethicone with an antacid, antidiarrheal or an antiperistaltic agent to provide lessening of gastrointestinal pain. See for example, EP-A-0428296 and EP-A-0014253. Nevertheless, when formulating simethicone with antidiarrheals, antiperistaltic and histamine H2 antagonist, it has been discovered that without taking special precautions, the speed of dissolution of the antidiarrheals, antiperistaltic and histamine H2 antagonist occurs in an adverse manner.

OBJECTS OF THE INVENTION

It is therefore a primary object of the present invention to provide a composition for the treatment of gastrointestinal distress.

Another object of the invention is to provide a pharmaceutical composition for treating gastrointestinal distress, containing an effective amount of an antidiarrheal compound combined with an antiflatulent effective amount of simethicone.

A still further object of the invention is to provide a pharmaceutical composition comprising: (a) an effective amount of an intestinal motility regulating agent which has an agonist effect on peripheral µ, d and k opiate receptors; (b) an effective amount of an antiflatulent.

Yet, another object of the invention is to provide granular pharmaceutical compositions comprising in combination effective amounts of trimebutine and effective amounts of simethicone.

Accordingly, a main object of the present invention is to avoid the disadvantages of the previous art. More in particularly, a main object of the present invention is to create a pharmaceutical composition for the treatment and regulation in mammals of intestinal digestive motility and/or flatulence using trimebutine in combination with simethicone.

SUMMARY OF THE INVENTION

The present invention provides a solid pharmaceutical composition comprising: (a) an effective amount of an intestinal motility regulating agent which has an agonist effect on peripheral µ, d and k opiate receptors; (b) an effective amount of an antiflatulent; and (c) a pharmaceutically acceptable inert excipient.

The instant invention also provides a granular pharmaceutical composition comprising in combination effective amounts of trimebutine and effective amounts of simethicone.

The invention is also directed to a composition for treating a human suffering from an intestinal disorder by the symptoms of diarrhea and flatulence or gas comprising: an effective amount of trimebutine, stereoisomers thereof and metabolites thereof and their pharmaceutically acceptable salts and mixtures thereof; and an antiflatulent effective amount of simethicone.

The present invention further provides a method for treating a human suffering from an intestinal disorder characterized by the symptoms of diarrhea and flatulence or gas comprising administering to said human in a combined pharmaceutical composition, an effective amount of trimebutine, stereoisomers of trimebutine and metabolites thereof and its pharmaceutically acceptable salts; and an antiflatulent effective amount of simethicone.

In accordance with the present invention, we have discovered a solid oral dosage form for the treatment of gastrointestinal disorders containing trimebutine and simethicone.

DETAILED DESCRIPTION OF THE INVENTION

The present invention relates to a pharmaceutical composition that includes (a) at least a digestive motility regulating agent; (b) at least an antiflatulence agent; (c) at least a flow promoter; (d) one or more lubricant; (e) at least an extender/diluent; (f) at least a disintegrant; and, (g) at least a binder. According to the present invention, the motility regulating agent is trimebutine and the antiflatulence agent is simethicone. The composition of the present invention is useful for the treatment and regulation of digestive and/or instentinal motility and flatulence in mammals.

To achieve the object of the invention of providing a pharmaceutical composition for treating gastrointestinal distress, an effective amount of an intestinal motility regulating agent which has an agonist effect on peripheral µ, δ and κ opiate receptors is combined with an antiflatulent effective amount of simethicone.

The preferred antiflatulent composition combined with effective amounts of the intestinal motility regulating composition in accordance with the invention is simethicone, also known as polydimethylsiloxane and having the following chemical structure:

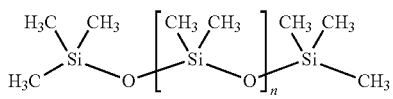

wherein n is an integer from about 1 to about 200, more preferably 7 to about 15.

Thus, simethicone is a mixture of fully methylated linear siloxane polymers containing repeating units of polydimethylsiloxane stabilized with trimethylsiloxy end-blocking units, and silicon dioxide. Simethicone contains 90.5-99% of polydimethylsiloxane and 4-7% silicon dioxide. The polydimethylsiloxanes present in simethicone are practically inert polymers having a molecular weight of 14,000-21,000. The mixture is a gray, translucent, viscous fluid which is insoluble in water.

When administered orally, simethicone is used as an adjunct in the symptomatic treatment of flatulence, functional gastric bloating, and postoperative gas pains. Simethicone is a surface active agent which acts as a defoamer or dispersant of gas bubbles by changing the surface tension of the bubbles to enable them to coalesce. The defoaming action of simethicone relieves flatulence by dispersing and preventing the formation of mucous surrounded gas pockets in the gastrointestinal tract. By reducing the size of the gas bubbles, the gas is free to travel through the gastrointestinal tract for release by belching or passing flatus. This release thus relieves the pain and pressure commonly associated with the presence of gas in the gastrointestinal tract.

Simethicone acts largely in the stomach but is also believed to have gas relieving effect in the intestines. Since simethicone is not absorbed or metabolized by the body, if released in the stomach area, it will proceed through the gastrointestinal tract into the intestines. In preferred embodiments of the composition of the invention, simethicone is presented in an immediate release form that is released in the stomach area. Enteric coated simethicones or a combination of immediate release and enteric coated simethicones may be included in accordance with the present invention to release the simethicone in the intestines.

The preferred dosage ranges for simethicone is in the range of about 20 to 125 mg. per dosage unit, generally not to exceed 500 mg/day. The dosage ranges may vary with age and weight of a patient as well as the severity of symptoms.

In the context of the present invention, the preferred motility regulating agent is trimebutine and as such it is provided in the pharmaceutical composition for preventing and/or treating gastrointestinal distress.

Trimebutine has the following chemical structure:

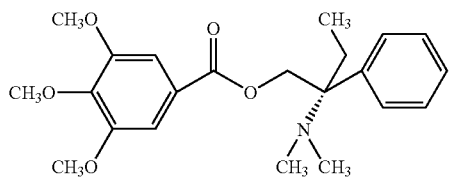

Pharmaceutical compositions include trimebutine and/or its corresponding stereoisomers including their salts and is produced by formulating the active compound in combination with simethicone in dosage unit form with at least one solid or liquid pharmaceutical acceptable carrier or excipient. Where it is appropriate to form a salt, the pharmaceutically acceptable salts include acetate, benzenesulfonate, benzoate, bitartrate, calcium acetate, camsylate, carbonate, citrate, edetate, edisylate, estolate, esylate, fumarate, gluceptate, gluconate, glutamate, glycoloylarsanilate, hexylresorcinate, hydrabamine, hydrobromide, hydrochloride, hydrogencarbonate, hydroxynaphthoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemi-succinate, sulfate or hemi-sulfate, tannate, tartrate or hemi-tartrate, theoclate, triethiodide, benzathine, chloroprocaine, choline, diethanolamine, ethylenediamine, meglumine, procaine, aluminum, ammonium, tetramethyl ammonium, calcium, lithium, magnesium, potassium, sodium, and zinc. (See also "Pharmaceutical salts" by Berge S. M. et al. (1997) J. Pharm. Sci. 66: 1-19, which is incorporated herein by reference.)

The preferred dosage ranges for trimebutine or its pharmaceutical acceptable salts is in the range of about 100 to 300 mg. per dosage unit, generally not to exceed 600 mg/day. The dosage ranges may vary for age and weight of a patient as well as the severity of symptoms.

The oral pharmaceutical dosage forms of the invention are solid forms. The solid dosage forms are tablets, capsules, granules and bulk powders. Types of oral tablets are, for example, compressed (including chewable and lozenge), tablet triturates, enteric-coated, sugar-coated, film-coated, and multiple compressed. Capsules are either hard or soft elastic gelatin. Granules and powders are either effervescent or non-effervescent.

Pharmaceutically acceptable substances utilized in compressed tablets are binders, lubricants, diluents, extender/diluents, disintegrating agents, coloring agents, flavoring agents, flow inducing/promoting agents, and wetting agents. Tablet triturates (either molded or compressed) utilize diluents and binders. Enteric-coated tablets, due to their enteric-coating, resist the action of stomach acid and dissolve or disintegrate in the alkaline intestine. Sugar-coated tablets are compressed tablets to which usually four different layers of pharmaceutically acceptable substances have been applied. Film-coated tablets are compressed tablets which have been coated with a water soluble cellulose high polymer. Multiple compressed tablets are compressed tablets made by more than one compression cycle utilizing the pharmaceutically acceptable substances previously mentioned. Coloring agents are utilized in all the above dosage forms. Flavoring and sweetening agents are utilized in compressed tablets, tablet triturates, sugar coated, multiple compressed and chewable tablets. Flavoring and sweetening agents are especially useful in the formation of chewable tablets and lozenges.

Solid dosage forms for oral administration include capsules, tablets, pills, powders, and granules. In such solid dosage forms, the active component is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alginates, gelatin, polyvinylpyrrolidone, sucrose, and acacia, (c) humectants, as for example, ethanol and/o glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose as well as high molecular weight polyethyleneglycols, and the like.

Of course, additionally, the compositions of the present invention may be formulated in sustained release form to provide the rate controlled release of any one or more of the components to optimize the therapeutic effects, i.e., analgesia, skeletal muscle relaxation, etc. while minimizing undesirable side effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Examples of binders include glucose solution (25-50%), acacia mucilage (10-20%), gelatin solution (10-20%), sucrose and starch paste. Lubricants include, for example, talc, starch, magnesium or calcium stearate, lycopodium and stearic acid. Diluents include, for example, lactose, sucrose, starch, kaolin, salt, mannitol, and dicalcium phosphate. Disintegrating agents include, for example, corn starch, potato starch, bentonite, methylcellulose, agar, and carboxymethylcellulose. Coloring agents include, for example, any of the approved certified water soluble FD and C dyes, mixtures thereof, and water insoluble FD and C dyes suspended on alumia hydrate. Sweetening agents include, for example, sucrose, lactose, mannitol, and artificial sweetening agents such as sodium cyclamate and saccharin, and any number of spray dried flavors. Flavoring agents include natural flavors extracted from plants such as fruits and synthetic blends of compounds which produce a pleasant sensation. Flow inducing agents include, for example, silicon dioxide and talc. Wetting agents include, for example, propylene glycol monostearate, sorbitan monooleate, diethylene glycol monolaurate, and polyoxyethylene laural ether. Enteric-coatings include, for example, fatty acids, fats, waxes, shellac, ammoniated shellac and cellulose acetate phthalates. Pharmaceutically acceptable substances for the first layer, an undercoating, of sugar-coated tablets include, for example, dextrin and gelatin. The second layer, an opaque zone, includes, for example, starch, talc, calcium carbonate, magnesium oxide, and magnesium carbonate. The third layer, a translucent zone, includes, for example, sucrose. The fourth layer, a glaze, includes, for example, beeswax, carnauba wax, or a mixture of these waxes. Film coatings include, for example, hydroxyethylcellulose, sodium carboxymethylcellulose, polyethylene glycol 4000 and cellulose acetate phthalate.

Hard gelatin capsules, sizes 5 through 000, are made largely from gelatin and may be either clear or colored. These capsules may be filled with either a powder or coated pellets (sustained release).

The diluents utilized in powder filled capsules are the same as those illustrated above for tablets. Pharmaceutically acceptable substances utilized for coating pellets include, for example, stearic acid, palmitic acid, glyceryl myristate, cetyl alcohol, fats, waxes, polymeric substances sensitive to small changes in pH of the gastrointestinal tract, polyvinyl alcohol, ethyl cellulose, and mixtures of beeswax, carnauba wax or bayverry wax with glyceryl monostearate.

Soft elastic gelatin capsules contain sufficient glycerin so that they are permanently flexible. Pharmaceutically acceptable liquid diluents used in soft elastic gelatin capsules are those which do not dissolve or harm the capsule and which are non-toxic, including, for example, corn oil, cottonseed oil, and polysorbate 80.

The pharmaceutically therapeutically active compounds are administered orally in unit-dosage forms or multiple-dosage forms. Unit-dose forms as used in the specification and claims refers to physically discrete units suitable for human and animal subjects and packaged individually as is known in the art. Each unit-dose contains a predetermined quantity of the therapeutically active compounds sufficient to produce the desired therapeutic effect, in association with the required pharmaceutical carrier, vehicle or diluent. Examples of unit-dose forms include individually packaged tablet or capsule (oral-solid), or individually packaged teaspoonful or tablespoonful (oral-liquid). Unit-dose forms may be administered in fractions or multiples thereof. A multiple-dose form is a plurality of identical unit-dosage forms packaged in a single container to be administered in segregated unit-dose form. Examples of multiple-dose forms include bottles of tablets or capsules (oral-solid), or bottles of pints or gallons (oral-liquid). Hence, multiple dose form is a multiple of unit-doses which are not segregated in packaging. The specifications for the unit-dosage form and the multiple-dosage form are dictated by and directly dependent on (a) the unique characteristics of the therapeutically active compounds and the particular therapeutic effect to be achieved and (b) the limitations inherent in the art of compounding such a therapeutically active compound for treatment of propylaxis of gastric and intestinal distress.

This invention is further directed to a solid pharmaceutical composition that includes a regulating agent of digestive motility and an antiflatulence agent antiflatulent for the treatment and regulation of the intestinal motility and flatulence in mammals. Particularly, the pharmaceutical composition includes: (a) at least a regulating agent of the motility; (b) at least an antiflatulence agent; (c) at least a flowability promoter; (d) one or more lubricant; (e) at least an extender/diluent; (f) at least a disintegrant; and, (g) at least a binder.

According to the present invention, the motility regulating agent is a regulating agent of intestinal motility such as trimebutine, stereoisomers of trimebutine and metabolites thereof and/or its pharmaceutically acceptable salts and the antiflatulence agent is simethicone. The intestinal motility regulating agent is present in this pharmaceutical composition, in an amount that can vary from 5% to 25% of the gross weight of the composition. More preferably, the agent regulating intestinal motility is trimebutine, and it is present in an amount of between about 10% to about 20% of the gross weight of the composition. On the other hand, the antiflatulence agent is present in an amount that can vary from about 20% to about 40% of the gross weight of the composition. Preferably the proportion of simethicone is between about 25% and about 35% of the gross weight of the composition.

Also, the composition includes a flow promoter. The flow promoter can be chosen from the group consisting of talc, starch, polyethyleneglycol 4000, silicon dioxide, microcrystalline cellulose or mixtures thereof. In order to facilitate the flowability, the flow promoter must be present in an amount from about 2% to about 10% of the gross weight of the composition. More preferably, according to the invention the flow promoter is present in an amount ranging from about 3% to about 6% of the gross weight of the composition.

The lubricants which are useful in the present invention are selected from the group consisting of talc, magnesium stearate, calcium stearate, stearic acid, sodium stearyl fumarate, hydrogenated vegetable oils, sodium benzoate, sodium chloride, leucine, polyethyleneglycol 4000, sodium lauryl sulphate and mixtures thereof. The preferred lubricants are selected of the group consisting of magnesium stearate, calcium stearate, sodium lauryl sulphate and mixtures thereof. According to the invention, the lubricants are present in an amount ranging from about 0.25% to about 8% of the gross weight of the composition. More preferably, the lubricants are present in an amount ranging from about 1% to about 6% of the gross weight of the composition.

Regarding the extender/diluents of the invention, the composition of the present invention in solid form, must include an amount ranging from about 5% to about 50% of the gross weight of the composition and said extender/diluents are selected from the group consisting of dicalcium phosphate, calcium sulphate, lactose monohydrate, kaolin, mannitol, sodium chloride, starch, pulverized sugar, microcrystalline cellulose and its derivatives, polyalcohols and mixtures thereof. More in particularly, the extender/diluent is present in an amount between about 10% to about 40% of the gross weight of the composition.

The disintegrant useful in the composition of the invention can be chosen from the group consisting of corn starch, potato starch, sodium carboxymethyl starch, pregelatinized starch, sodium croscarmellose, methylcellulose, bentonite, veegum, ion exchange resins, alginic acid, guar gum, carboxymethylcellulose, sodium lauryl sulphate, starch glycolate, microcrystalline cellulose, polyvinylpyrrolidone, cross-linked polyvinylpyrrolidone and mixtures thereof. The above disintegrants are added to the composition of the instant invention in an amount between about 2% to about 9% of the gross weight of the composition and more preferably, it is present in an amount between about 5% to about 8% of the gross weight of the composition.

The composition of to the invention also includes a binder which is selected from the group consisting of starch, gelatin, sucrose, glucose, dextrose, lactose, polyvinylpyrrolidone, gum acacia, sodium alginate, carboxymethylcellulose, methylcellulose, veegum, polyethyleneglycol 4000, polyethyleneglycol 6000, ethylcellulose, waxes, gum tragacantt, agar-agar, pectine, dextrin, polyvinyl alcohol, carbopol, bentonite, kaolin and mixtures thereof.

Also, the binder provides a humectant effect to the composition of the invention. The binder is present in the composition in an amount from about 2% to about 8% of the gross weight of the composition, preferably in an amount from about 4% to about 7% of the gross weight of the composition.

According to the present invention, the pharmaceutical composition can be in the form of granules, a reconstitutable powder for suspension, as microgranules, chewable tablet, coated tablets or a gelatin capsule. In a preferred embodiment of the invention, the pharmaceutical composition is in the form of a coated tablet. With respect to the coated pharmaceutical tablet of the invention, the solid form includes: (a) a tablet core that includes therapeutically a effective dose of at least a an intestinal motility regulating agent motility and at least an antiflatulence agent, at least one or more lubricant, a flowability promoter, at least an extender/diluent, at least a disintegrant and at least a binder; and, (b) an external coating. In the embodiment of the coated tablet, the tablet core must contain granules with a size between 250 μm and 6000 μm, preferably between 400 μm and 4000 μm. The core is made up of trimebutine, simethicone, and suitable additional excipients for the production of the granule. According to the present invention the dual action by using the combination between trimebutine and simethicone, produces synergy which is complementary to one another. Both substances are safe and simethicone is a medicine approved by the FDA since 1952. Also, we have found that the medicine is not absorbed therefore it does not have sistemic but local action. Aside from its effects on surface tension, simethicone can stimulate the gastrointestinal motility and therefore accelerate the propulsion and expulsion of the gas.

The film coating is formed on at least a portion, preferably on all, of the exposed surface of the core containing the pharmaceutical actives. The film forming agent is typically a water/ethanol soluble film forming polymer, such as hydroxypropyl methylcellulose, methylcellulose, ethylcellulose, hydroxypropyl cellulose, povidone, polydextrose, lactose, maltodextrin, acrylic polymer, and mixtures thereof. The film coating may optionally contain a plasticizer, such as castor oil, polyethylene glycol, propylene glycol or glycerine, and a coloring or opacifying agent. The film coating may also contain a flavoring and/or sweetening agent to improve palatability. A preferred blend of hydroxypropyl methylcellulose, a plasticizer and a colorant is commercially available from Colorcon, West Point, Pa. under the tradename Opadry White OY-S-7322

As stated above, the preferred form of the invention is a solid dosage form in the form of a tablet more preferably a coated tablet. The tablet depending on the desired effective amounts typically contains the amounts shown in Table 1.

TABLE 1

| Component | Amount mg |
| --- | --- |
| Colloidal Silica (Aerosil 200) | 30-60 mg |
| Trimebutine maleate | 100-200 mg |
| Magnesium stearate | 18.75-37.5 mg |
| Powder simethicone (30%) | 200-400 mg |
| Talc | 10-20 mg |
| Sodium starch glycolate | 40-80 mg |
| Sodium lauryl sulfate | 7.5-15 mg |
| FD &C Yellow #10 | 0.045-0.09 mg |
| Polyvinylpyrrolidone K-90 | 35-70 mg |
| Lactose monohydrate | 189-368 mg |

The above tablet is coated with a composition as shown in table 2.

TABLE 2

| Component | Amount |
| --- | --- |
| Opadry White OY-S-7322 | 34-68 mg |
| FD&C Yellow #10 | 0.015-0.030 mg |
| Ethyl alcohol USP | 300-600 mg |

The present invention also provides a method of treating gastrointestinal distress. The method comprises administering a combination pharmaceutical composition in accordance with the invention to a patient having the symptoms of gastrointestinal distress which is a combination of diarrhea and flatulence, including discomforts associated with flatulence which may include bloating, pain, and uncomfortable fullness. The method comprises treating the patient with an effective amount of an antidiarrheal composition and an antiflatulent effective amount of simethicone. The antidiarrheal is preferably trimebutine. More preferably, the antidiarrheal composition is trimebutine maleate in a dosage range of about 100 mg to about 300 mg. combined with from about 20 to about 175 mg. of simethicone.

EXAMPLES

The following procedure is used throughout the examples below to make the granulate and tablets of the invention.

In a mixer the following materials are mixed thoroughly for 30 minutes: trimebutine maleate, powdered simethicone (30%), sodium starch glycolate (50% of the total in the formulation), lactose monohydrate, silicon dioxide (aerosol 200), and polyvinylpyrrolidone (K-90).

To the above mixed mixture of ingredients, there is added with agitation the FD&C yellow #10 and ethyl alcohol so as to obtain a dough/paste which is adequate for granulation. The moist dough/paste is then subjected to granulation in a granulator equipped with a No. 4 screen and the resulting granulate is placed in drying trays. The trays containing the moist granulate are placed in an oven for a period of 12-24 hours at 45° C.±5° C. or until all the alcohol is evaporated.

The dry granulate is further broken down a sieved through a No. 14 screen and placed in a mixer and mixed for 15 minutes with talc, sodium lauryl sulfate and sodium starch glycolate. Magnesium stearate is then added and the mixture is further mixed for five minutes. The resulting mix is now ready for use to make tablets using conventional tablet compression equipment.

The resulting tablets are then coated using conventional tablet coating techniques with a coating composition containing ethyl alcohol, Opadry White OY-S-7322 and F D &C Yellow No. 10.

The following are representative formulations of the invention.

Example 1

| Component | Amount mg |
| --- | --- |
| Colloidal Silica (Aerosil 200) | 30 mg |
| Trimebutine maleate | 100 mg |
| Magnesium stearate | 18.75 mg |
| Powder simethicone (30%) | 200 mg |
| Talc | 10 mg |
| Sodium starch glycolate | 40 mg |
| Sodium lauryl sulfate | 7.5 mg |
| FD &C Yellow #10 | 0.045 mg |
| Polyvinylpyrrolidone K-90 | 35 mg |
| Lactose monohydrate | 189 mg |

Example 2

| Component | Amount mg |
| --- | --- |
| Colloidal Silica (Aerosil 200) | 45 mg |
| Trimebutine maleate | 150 mg |
| Magnesium stearate | 25 mg |
| Powder simethicone (30%) | 300 mg |
| Talc | 15 mg |
| Sodium starch glycolate | 60 mg |
| Sodium lauryl sulfate | 10 mg |
| FD &C Yellow #10 | 0.06 mg |
| Polyvinylpyrrolidone K-90 | 55 mg |
| Lactose monohydrate | 270 mg |

Example 3

| Component | Amount mg |
| --- | --- |
| Colloidal Silica (Aerosil 200) | 60 mg |
| Trimebutine maleate | 200 mg |
| Magnesium stearate | 37.5 mg |
| Powder simethicone (30%) | 400 mg |
| Talc | 20 mg |
| Sodium starch glycolate | 80 mg |
| Sodium lauryl sulfate | 15 mg |
| FD &C Yellow #10 | 0.09 mg |
| Polyvinylpyrrolidone K-90 | 70 mg |
| Lactose monohydrate | 368 mg |

Example 4

| Component | Amount mg |
| --- | --- |
| Colloidal Silica (Aerosil 200) | 50 mg |
| Trimebutine maleate | 175 mg |
| Magnesium stearate | 30 mg |
| Powder simethicone (30%) | 300 mg |
| Talc | 18 mg |
| Sodium starch glycolate | 70 mg |
| Sodium lauryl sulfate | 12 mg |
| FD &C Yellow #10 | 0.06 mg |
| Polyvinylpyrrolidone K-90 | 60 mg |
| Lactose monohydrate | 300 mg |

Some preferred embodiments of the invention have been described however they are not intended to be limiting. In this respect, it will be appreciated that the solid pharmaceutical composition that includes in combination a regulating agent of intestinal motility and an antiflatulence agent, can be chosen of a plurality of alternatives without departing from the spirit of the invention according to the subjoined claims.

Although the present invention has been described with reference to specific details of certain embodiments thereof, it is not intended that such detail should be regarded as limitations upon the scope of the invention, except as and to the extent that they are included in the accompanying claims.

What is being claimed is:

1. A solid pharmaceutical composition consisting of: (a) an effective amount of an intestinal motility regulating agent selected from the group consisting of trimebutine, trimebutine maleate, stereoisomers of trimebutine and metabolites thereof; (b) an effective amount of simethicone; and (c) a pharmaceutically acceptable inert excipient consisting of: (i) 2-10% by weight of a flowability promoting agent selected from the group consisting of: talc, starch, polyethyleneglycol 4000, silicon dioxide, microcrystalline cellulose and mixtures thereof; (ii) 0.25% to about 8% by weight of a lubricant selected of the consisting of talc, magnesium stearate, calcium stearate, stearic acid, sodium steary fumarate, hydrogenated vegetable oils, sodium benzoate, sodium chloride, leucine, polyethyleneglycol 4000, sodium laury sulphate and mixtures thereof; (iii) 5% to about 50% by weight of an extender/diluent selected from the group consisting of dicalcium phosphate, calcium sulphate, lactose monohydrate, kaolin, mannitol, sodium chloride, starch, pulverized sugar, microcrystalline cellulose and its derivatives, polyalcohols or mixtures thereof; (iv) 2% to about 9% by weight of a disintegrant selected from the group consisting of corn starch, potato starch, sodium carboxymethyl starch, pregelatinized starch, sodium croscarmellose, methylcellulose, bentonite, veegurn, ion exchange resins, alginic acid, guar gum, carboxymethylcellulose, sodium lauryl sulphate, starch glycolate, microcrystalline cellulose, polyvinylpyrrolidone, crossliked polyvinylpyrrolidone and mixtures thereof; (v) 2% to about 8% by weight of a binder selected from the group consisting of starch, gelatin, sucrose, glucose, dextrose, lactose, polyvinylpyrrolidone, acacia gum, sodium alginate, carboxymethylcellulose, methylcellulose, veegum, polyethyleneglycol 4000, polyethyleneglycol 6000, ethylcellulose, waxes, tragacanth gum, to agar-agar, pectin, dextrin, polyvinyl alcohol, carbopol, bentonite, kaolin and mixtures thereof; said solid composition being formed from granules having a particle size in the range between 250 µm and 6000 µm.

2. The solid pharmaceutical composition according to claim 1 wherein the intestinal motility regulating agent is trimebutine maleate.

3. The solid pharmaceutical composition according to claim 2 wherein the trimebutine maleate is present in the range from about 5% to about 25% of the gross weight of the composition, and the simethicone is present in the range from about 20% to about 40% of the gross weight of the composition.

4. The solid pharmaceutical composition according to claim 3 wherein the trimebutine maleate is present in the range from about 10% to about 20% of the gross weight of the composition, and the simethicone is present in the range from about 25% to about 35% of the gross weight of the composition.

5. The solid pharmaceutical composition according to claim 1 wherein the flowability promoting agent is present in an amount from about 3% to about 6% of the gross weight of the composition.

6. The solid pharmaceutical composition according to claim 1 where said lubricant is present in an amount from about 1% to about 6% of the gross weight of the composition.

7. The solid pharmaceutical composition according to claim 1, wherein the extender/diluent is present in an amount from about 10% to about 40% of the gross weight of the composition.

8. The solid pharmaceutical composition according to claim 1, wherein the disintegrant is present in an amount from about 5% to about 8% of the gross weight of the composition.

9. The solid pharmaceutical composition according to claim 1, wherein said binder is present in an amount from about 4% to about 7% of the gross weight of the composition.

10. The solid pharmaceutical composition according to claim 1, in an oral dosage form selected from the group consisting of a granulate, tablet, coated tablets, delayed release tablets, sustained release, chewable tablets, reconstitutable powder, hard and soft gelatin capsules, lozenge, syrup, suspension and elixir.

11. The solid pharmaceutical composition according to claim 10, wherein said oral dosage form is a coated tablet.

12. The solid pharmaceutical composition according to claim 11 wherein said coated tablet includes (a) a tablet core that includes a therapeutically effective dose of at least a regulating agent of intestinal motility and at least an antiflatulence agent, at least one or more lubricant, a flowability promoter, at least an extender/diluent, at least a disintegrant, at least a binder; and, (b) a coating.

13. A granular pharmaceutical composition consisting in combination effective amounts of trimebutine; effective amounts of simethicone and an a pharmaceutically acceptable inert excipient consisting of: (i) 2-10% by weight of a flowability promoting agent selected from the group consisting of: talc, starch, polyethyleneglycol 4000, silicon dioxide, microcrystalline cellulose and mixtures thereof; (ii) 0.25% to about 8% by weight of a lubricant selected of the group consisting of talc, magnesium stearate, calcium stearate, stearic acid, sodium stearyl fumarate, hydrogenated vegetable oils, sodium benzoate, sodium chloride, leucine, polyethyleneglycol 4000, sodium lauryl sulphate and mixtures thereof; (iii) 5% to about 50% by weight of an extender/diluent selected from the group consisting of dicalcium phosphate, calcium sulphate, lactose monohydrate, kaolin, mannitol, sodium chloride, starch, pulverized sugar, microcrystalline cellulose and its derivatives, polvalcohols or mixtures thereof; (iv) 2% to about 9% by weight of a disintegrant selected from the group consisting of corn starch, potato starch, sodium carboxvmethyl starch, pregelatinized starch, sodium croscarmellose, methylcellulose, bentonite, veegum, ion exchange resins, alginic acid, guar gum, carboxymethylcellulose, sodium lauryl sulphate, starch glycolate, microcrystalline cellulose, polyvinylpyrrolidone, cross-linked polyvinylpyrrloidone and mixtures thereof; (v) 2% to about 8% by weight of a binder selected from the group consisting of starch, gelatin, sucrose, glucose, dextrose, lactose, polyvinylpyrrolidone, acacia gum, sodium alginate, carboxymethylcellulose, methylcellulose, veegum, polyethyleneglycol 4000, polyethuyleneglycol 6000, ethylcellulose, waxes, tragacanth gum, to agar-agar, pectin, dextrin, polyvinyl alcohol, carbopol, bentonite, kaolin and mixtures thereof; said composition having a particle size in the range between 400 µm and 4000 µm.

14. A composition for treating a human suffering from an intestinal disorder characterized by the symptoms of diarrhea and flatulence or gas consisting of: an effective amount of trimebutine, stereoisomers thereof and metabolites thereof and their pharmaceutically acceptable salts and mixtures thereof; an antiflatulent effective amount of simethicone; and an a pharmaceutically acceptable inert excipient consisting of:(i) 2-10% by weight of a flowability promoting agent selected from the group consisting of: talc, starch, polyethyleneglycol 4000, silicon dioxide, microcrystalline cellulose and mixtures thereof; (ii) 0.25% to about 8% by weight of a lubricant selected of the group consisting of talc, magnesium stearate, calcium stearate, stearic acid, sodium stearyl fumarate, hydrogenated vegetable oils, sodium benzoate, sodium chloride, leucine, polyethyleneglycol 4000, sodium lauryl sulphate and mixtures thereof; (iii) 5% to about 50% by weight of an extender/diluent selected from the group consisting of dicalcium phosphate, calcium sulphate, lactose monohydrate, kaolin, mannitol, sodium chloride, starch, pulverized sugar, microcrystalline cellulose and its derivatives, polyalcohols or mixtures thereof; (iv) 2% to about 9% by weight of a disintegrant selected from the group consisting of corn starch, potato starch, sodium carboxymethyl starch, pregelatinized starch sodium croscarmellose, methylcellulose, bentonite, veegum, ion exchange resins, alginic acid, guar gum, carboxymethylcellulose, sodium lauryl sulphate, starch glycolate, microcrystalline cellulose, polyvinylpyrrolidone, cross-linked polyvinylpyrrolidone and mixtures thereof; (v) 2% to about 8% by weight of a binder selected from the group consisting of starch, geltin, sucrose, glucose, dextrose, lactose, polyvinylpyrrolidone, acacia gum, sodium alginate, carboxymethylcellulose, methylcellulose, veegum, polyethyleneglycol 4000, polyethyleneglycol 6000, ethylcellulose, waxes, tragacanth gum, to agar-agar, pectin, dextrin, polyvinyl alcohol, carbopol, bentonite, kaolin and mixtures thereof; said composition being in granular form having a particle size in the range between 250 µm and 6000 µm.

15. A method for treating a human suffering from an intestinal disorder characterized by the symptoms of diarrhea and flatulence or gas comprising administering to said human in a combined pharmaceutical composition, an effective amount of trimebutine, stereoisomers of trimebutine and metabolites thereof and its pharmaceutically acceptable salts; an antiflatulent effective amount of simethicone; and an a pharmaceutically acceptable inert excipient consisting of: (i) 2-10% by weight of a flowability promoting agent selected from the group consisting of: talc, starch, polyethyleneglycol 4000, silicon dioxide, microcrystalline cellulose and mixtures thereof; (ii) 0.25% to about 8% by weight of a lubricant selected of the group consisting of talc, magnesium stearate, calcium stearate, stearic acid, sodium stearyl fumarate, hydrogenated vegetable oils, sodium benzoate, sodium chloride, leucine, polvethyleneglycol 4000, sodium lauryl sulphate and mixtures thereof; (iii) 5% to about 50% by weight of an extender/diluent selected from the group consisting of dicalcium phosphate, calcium sulphate, lactose monohydrate, kaolin, mannitol, sodium chloride, starch, pulverized sugar, microcrystalline cellulose and its derivatives, polyalcohols or mixtures thereof; (iv) 2% to about 9% b weight of a disintegrant selected from the group consisting of corn starch, potato starch, sodium carboxymethyl starch, pregelatinized starch, sodium croscarmellose, methylcellulose, bentonite, veegum, ion exchange resins, alginic acid, guar gum, carboxymethylcellulose, sodium laurvl sulphate, starch glycolate, microcrystalline cellulose, polyvinylpyrrolidone, cross-linked polyvinylpyrrolidone and mixtures thereof; (v) 2% to about 8% by weight of a binder selected from the group consisting of starch, gelatin, sucrose, glucose, dextrose, lactose, polyvinylpyrrolidone, acacia gum, sodium alginate, carboxymethylcellulose, methylcellulose, veegum, polyethyleneglycol 4000, polyethyleneglycol 6000, ethylcellulose, waxes, tragacanth gum, to agar-agar, pectin, dextrin, polyvinyl alcohol, carbopol, bentonite, kaolin and mixtures thereof; said composition being in granular form having a particle size in the range between 250 μm and 6000 μm.

\* \* \* \* \*